US00PP32073P2

(12) United States Plant Patent
Hansen

(10) Patent No.: US PP32,073 P2
(45) Date of Patent: Aug. 11, 2020

(54) ***KNIPHOFIA* PLANT NAMED 'SOLAR FLARE'**

(50) Latin Name: *Kniphofia hybrida*
Varietal Denomination: Solar Flare

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 36 days.

(21) Appl. No.: 16/350,525

(22) Filed: Nov. 28, 2018

(51) Int. Cl.
*A01H 5/02* (2018.01)

(52) U.S. Cl.
USPC ..... Plt./443

(58) Field of Classification Search
USPC ..... Plt./443
CPC ..... A01H 5/02
See application file for complete search history.

*Primary Examiner* — Annette H Para

(57) ABSTRACT

A new and distinct cultivar of Red Hot Poker plant named *Kniphofia* 'Solar Flare' with long, gracefully-arching, strap-like, keeled, glaucous, gray-green foliage and numerous scapes beginning in early summer and repeating though early fall. Habit is densely-growing, winter-hardy and tolerant of heat. Numerous scapes with dense flowers of bright-yellow flowers. The new plant is useful for landscaping as a specimen, en masse, or as a long-lasting cut flower.

1 Drawing Sheet

Botanical classification: *Kniphofia hybrida.*
Variety denomination: 'Solar Flare'.

STATEMENT REGARDING PRIOR DISCLOSURES UNDER 37 CFR 1.77(B)(6)

The first public disclosure of the claimed plant, in the form of a sale, was made by Walters Gardens, Inc. on May 14, 2018. Prior to that, on Dec. 1, 2017 the claimed plant was displayed with a photograph and brief sales promotion on the website of Walters Gardens, Inc., who obtained the plant and all information relating thereto, from the inventor. No plants of *Kniphofia* 'Solar Flare' have been sold, in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to the new and distinct Red Hot Poker, *Kniphofia* 'Solar Flare' developed under the direction of the inventor at a wholesale perennial nursery in Zeeland, Mich., USA. The new plant was the result of a single seedling selection from a cross of 'Sally's Comet' (not patented) as the female or seed parent and 'Echo Mango' U.S. Plant Pat. No. 21,706 as the male or pollen parent on Jul. 9, 2013. The plant passed initial evaluation in the summer of 2015 and was subsequently given the breeder code 13-4-7 prior to naming. *Kniphofia* 'Solar Flare' has been successfully asexually propagated by division method since 2015 at the same wholesale perennial nursery in Zeeland, Mich. and subsequently by shoot tip tissue culture, and both methods have been found to be stable and produce identical plants that maintain the unique characteristics of the original plant through successive generations.

SUMMARY OF THE PLANT

*Kniphofia* 'Solar Flare' differs from its parents as well as all other *Kniphofia* known to the applicant. The most similar known *Kniphofia* cultivars are the female parent 'Sally's Comet', 'Flashpoint' co-pending U.S. Plant Patent Application and 'Banana Popsicle' U.S. Plant Pat. No. 27,617. 'Banana Popsicle' is much shorter in scape and foliage height with fewer flowers per inflorescence. 'Flashpoint' is slightly taller in scape height, foliage height and overall habit and has a lighter chartreuse-yellow flower buds and cream flowers later in the summer. 'Sally's Comet' has green buds five days prior to opening and chartreuse buds one day prior to opening, and the plant is slightly shorter in habit. 'Echo Mango' is more apricot-orange-colored in flower.

*Kniphofia* 'Solar Flare' differs from these above cultivars and all cultivars known to the inventor in that it has:

1. Gracefully arching, strap-like, keeled, gray-green foliage.
2. Rapidly growing, dense habit, winter-hardy, heat tolerant, and moderate-sized clumps.
3. Numerous spikes of bright-yellow flowers medium height stems;
4. Flowering beginning early-summer and repeating into early October in Michigan.

BRIEF DESCRIPTION OF THE DRAWINGS

The photographs of *Kniphofia* 'Solar Flare' demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
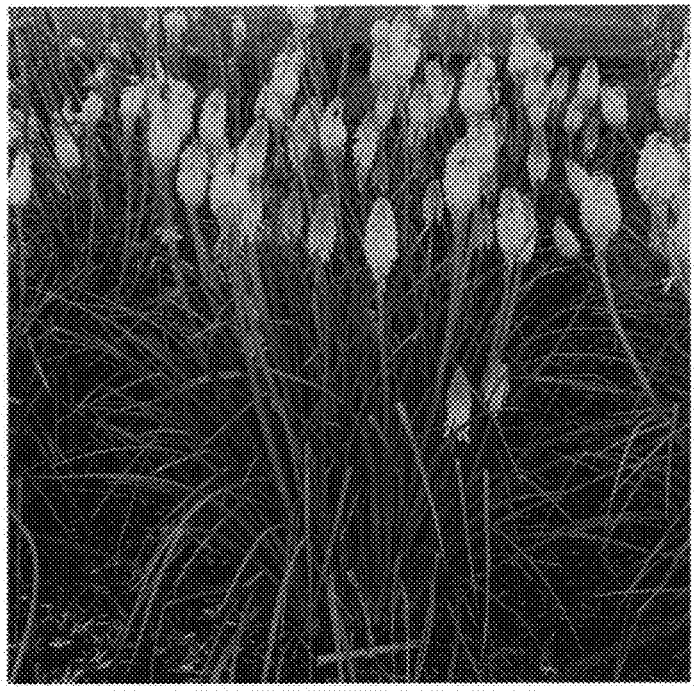
FIG. 1 shows the side-view habit of a five-year-old plant in midseason flowering.
Figure 2:
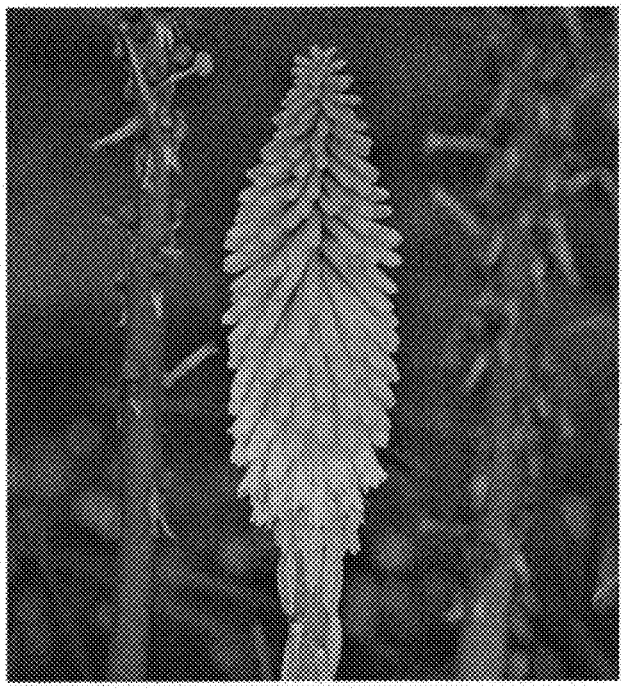
FIG. 2 shows a close-up of the flowers and buds.

The following descriptions and color references are based on the 2015 edition of The Royal Horticultural Society Colour Chart except where common dictionary terms are used. The new plant, *Kniphofia* 'Solar Flare', has not been observed under all possible environments. The phenotype may vary slightly with different environmental conditions, such as temperature, light, fertility, moisture and maturity levels, but without any change in the genotype. The following observations and size descriptions are of a five-year-old plant in a trial garden of a wholesale perennial nursery in Zeeland, Mich. under full sun with supplemental water and fertilizer as needed.

Botanical classification: *Kniphofia* hybrid;

Parentage: *Kniphofia* 'Sally's Comet' as the female or seed parent and 'Echo Mango' plant as the male or pollen parent;

Propagation method: By garden division of the rhizome and shoot tip tissue culture;

Growth rate: Vigorous, flowering in 3.5 liter containers in about 10 to 12 weeks from a 25 mm plug liner in late winter to spring and from a one-year-old bare root plant to flowering in 6 to 8 weeks in a 4.0 liter container;

Rooting habit: Fibrous from base of rhizomes, lightly branching; color nearest RHS 158C;

Plant description: Dense, rhizomatous, acaulescent, perennial clump with long thin foliage to about 114.0 cm across and about 90.0 cm tall; flowering to about 97.0 cm tall; about 52 peduncles per plant;

Leaves: Linear; keeled at base, triangular in distal half; arranged about 8 leaves per basal division; apex narrowly acute; base truncate, clasping; margin entire; no fragrance observed;

Leaf size: To about 89.0 cm long and 25.0 mm across at base, average about 80.0 cm long and 20.0 mm across at base;

Leaf color: Young base nearest RHS 155A both abaxial and adaxial, distally between RHS 138B and RHS 138A both abaxial and adaxial; mature adaxial nearest RHS 146C and abaxial nearest RHS 146B;

Leaf venation: Parallel; color same as leaf abaxial and adaxial;

Stem: Short acaulescent rhizome about 22.0 mm across at base;

Inflorescence: In spike-like raceme; cylindrical; about 120 flowers per stem; flowering portion to about 20.0 cm tall and about 6.0 cm across; lasting about three weeks; flower spacing less than 1.0 mm apart on raceme in distal region and about 2.5 cm in lowest flowers;

Peduncle: Terete; glabrous; glaucous; solid not fistulose; to about 97.0 cm long and 13.0 mm diameter; taller in earlier season flowering; average 77.0 cm tall and 10.0 mm diameter;

Peduncle color: Nearest RHS N144A;

Buds one day prior to opening: Obellipsoidal, tubular with swollen subacute apex and rounded base; glabrous; lustrous; about 24.0 mm long and about 3.0 mm diameter at base and 5.0 mm diameter at widest point near apex;

Bud attitude: Beginning outwardly and drooping as maturing toward anthesis;

Bud color: Abaxial distal and dorsal portions one and five days prior to opening nearest RHS 7B with midrib nearest RHS 9A;

Flowers: Cylindrical forming tubular corolla; perfect; actinomorphic; individually open and effective about three to four days;

Flower size: To about 32.0 mm long to tip of exserted stamens and 8.0 mm across at apex; fused in basal about 24.0 mm; tube about 3.0 mm diameter near base and about 5.0 mm near throat; corolla tube to 27.0 mm long;

Flower attitude: Drooping;

Flower fragrance: None detected;

Flowering period: Individual racemes effective for about 3 weeks; beginning early summer Michigan for about six week, then continuing with repeat racemes until early fall with a short two week break in the heat of the summer;

Tepals: Six, in two sets of three; both sets with acute apices and fused in basal 24.0 mm forming tube; margin entire; glabrous and lustrous abaxial and adaxial; about 27.0 mm long and about 3.0 mm across just above fusion point;

Tepal color: Abaxial both outer and inner sets nearest RHS 4C with midribs nearest RHS 4A; rest RHS 1D; adaxial both outer and inner tepal sets nearest RHS 11B; abaxial and adaxial 1.0 wide distal margins nearest RHS 11D;

Androecium: Six; variable lengths;

*Filaments*.—Six; exserted; cylindrical; glabrous; lustrous; from about 27.0 to 31.0 mm long and about 0.5 mm diameter; color nearest RHS 4D.

*Anther*.—Slightly flattened ellipsoidal; dorsifixed; longitudinal; flattened ventrally to dorsally; about 2.0 mm long and 1.5 mm across and 1.0 mm thick; color nearest RHS 17B on dorsal side and nearest RHS 13A ventral side.

*Pollen*.—Abundant: color nearest RHS 12B.

Gynoecium: Single; about 28.0 mm long;

*Style*.—Cylindrical; glabrous; lustrous; about 26.0 mm long and 0.5 mm diameter: color nearest RHS 4C.

*Stigma*.—Flattened, round; about 0.3 mm across; color nearest RHS 4A.

*Ovary*.—Superior; dome-shaped; rounded apex, truncate base; about 2.0 mm long and 1.5 mm diameter; color nearest RHS 13B.

Pedicel: Cylindrical; glabrous; stiff; drooping with maturity; about 3.0 mm long and about 1.2 mm diameter;

Pedicel color: Nearest RHS 151D;

Bracts: Lanceolate to deltoid; at cauline nodes and subtending individual flowers; with acute apices and truncate base; average about 4.0 mm long and 3.0 mm across at base; decreasing distally; color translucent to nearest RHS 163D;

Fruit: Tri-valved loculicidal capsule; globose to ellipsoidal; about 7.5 mm long and 5.0 mm across; glabrous; with rounded apex and rounded base; with up to 21 seeds/pod; color upon maturity nearest RHS 200A;

Seed: Irregular with angular sides, acute apex and base; about 4.0 mm and 2.0 mm across; color nearest RHS 200A;

Disease and pest resistance: 'Solar Flare' does not tend to lodge, but other disease or pest resistance beyond that of other *Kniphofia* has not been observed. The plant grows best with good drainage and is able to tolerate some heat when established. Hardiness at least from USDA zone 6 through 9 and 5b with protection.

I claim:

1. A new and distinct cultivar of Red Hot Poker plant named *Kniphofia* 'Solar Flare' as herein described and illustrated.

* * * * *